US008449885B2

(12) United States Patent
Meng et al.

(10) Patent No.: US 8,449,885 B2
(45) Date of Patent: May 28, 2013

(54) ANTI-VEGF ANTIBODIES

(75) Inventors: Yu-Ju G. Meng, Albany, CA (US); Kyu H. Hong, Newark, CA (US); Johnny Gutierrez, Johnstown, CO (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 12/817,827

(22) Filed: Jun. 17, 2010

(65) Prior Publication Data

US 2010/0255515 A1    Oct. 7, 2010

Related U.S. Application Data

(63) Continuation of application No. 11/866,560, filed on Oct. 3, 2007, now abandoned.

(60) Provisional application No. 60/828,203, filed on Oct. 4, 2006.

(51) Int. Cl.
| | |
|---|---|
| *A61K 39/00* | (2006.01) |
| *A61K 39/395* | (2006.01) |
| *C12N 5/12* | (2006.01) |
| *C12P 21/08* | (2006.01) |
| *C07K 16/32* | (2006.01) |

(52) U.S. Cl.
USPC .................... 424/138.1; 424/178.1; 435/330; 530/388.8; 530/391.3

(58) Field of Classification Search
None
See application file for complete search history.

(56) References Cited

U.S. PATENT DOCUMENTS

| | | | | |
|---|---|---|---|---|
| 6,020,473 A | * | 2/2000 | Keyt et al. ................. | 536/23.1 |
| 6,855,508 B2 | | 2/2005 | Fei et al. | |
| 7,078,382 B1 | | 7/2006 | Shen et al. | |

FOREIGN PATENT DOCUMENTS

| | | |
|---|---|---|
| JP | T H10-511557 | 11/1998 |
| JP | 11178593 A | 6/1999 |
| JP | 11-178593 | 7/1999 |
| JP | T 2003-515136 | 4/2003 |
| RU | 2271010 C2 | 2/2006 |
| WO | WO 97/08313 | 3/1997 |
| WO | 97/09313 | 6/1997 |
| WO | 01/36972 | 5/2001 |
| WO | WO 01/36972 | 5/2001 |

OTHER PUBLICATIONS

Keyt et al (J Biological Chemistry, 1996, 271:5638-5646, IDS).*
Jayson et al (J National Cancer Institute, 2002, 94:1484-1493).*
Biocarta, antibody product sheet, Apr. 25, 2001, 4 pages.*
Andreansky et al (Cancer Research, 1997, 57:1502-1509).*
Novus Biologicals, Inc., 2006 catalogue, "Mouse monoclonal anti-VEGF (5C3.F8)" pp. 1-4.*
"Mouse Monoclonal anti-VEGF (5C3.F8) (retrieved from the internet)" *Novus Biologicals* pp. 1-4 (2006).
Aiello et al., "Vascular endothelial growth factor in ocular fluid of patients with diabetic retinopathy and other retinal disorders" *New England J. of Medicine* 331(22):1480-1487 (Dec. 1, 1994).
Anthony et al., "Variation in detection of VEGF in material serum by immunoassay and the possible influence of binding proteins" *Ann Clin Biochem.* 34:276-280 (1997).
Baccala et al., "Serum vascular endothelial growth factor is a candidate biomarker of metastatic tumor response to ex vivo gene therapy of renal cell cancer" *Urology* 51(2):327-332 (1998).
Baker et al., "Elevated serum levels of vascular endothelial growth factor in patients with preeclampsia" *Obstet. & Gynecol.* 86(5):815-821 (Nov. 1995).
Berkman et al., "Expression of the vascular permeability factor/vascular endothelial growth factor gene in central nervous system neoplasms" *J. Clin. Invest.* 91:153-159 (Jan. 1993).
Brekken et al., "Vascular Endothelial Growth Factor as a Marker of Tumor Endothelium" *Cancer Research* 58:1952-1959 (May 1, 1998).
Brown et al., "Expression of vascular permeability factor (vascular endothelial growth factor) and its receptors in adenocarcinomas of the gastrointestinal tract" *Cancer Research* 53:4727-4735 (Oct. 1, 1993).
Brown et al., "Expression of vascular permeability factor (vascular endothelial growth factor) and its receptors in breast cancer" *Human Pathology* 26(1):86-91 (1995).
Dvorak et al., "Vascular permeability factor/vascular endothelial growth factor, microvascular hyperpermeability, and angiogenesis" *American Journal of Pathology* 146(5):1029-1039 (May 1995).
Ferrara et al., "Vascular endothelial growth factor: basic science and clinical progress" *Endocr Rev.* 25(4):581-611 (Aug. 2004).
Ferrari and Scagliotti, "Serum and urinary vascular endothelial growth factor levels in non-small cell lung cancer patients" *European Journal of Cancer* 32A(13):2368-2369 (1996).
Fujisaki et al., "Circulating vascular endothelial growth factor in patients with colorectal cancer" *American Journal of Gastroenterology* 93(2):249-252 (1998).
Gasparini et al., "Prognostic significance of vascular endothelial growth factor protein in node-negative breast carcinoma" *Journal of National Cancer Institute* 89(2):139-147 (Jan. 15, 1997).
Gutierrez, J. et. al., "A New Elisa for Use in a 3-ELISA System to Assess Concentrations of VEGF Splice Variants and VEGF110 in Ovarian Cancer Tumors" *Clinical Chemistry* 54(3):597-601 (2008).
Hanatani et al., "Sensitive chemiluminescence enzyme immunoassay for vascular endothelial growth factor/vascular permeability factor in human serum" *Biosci. Biotech. Biochem.* 59(10):1958-1959 (1995).

(Continued)

*Primary Examiner* — Laura B Goddard
(74) *Attorney, Agent, or Firm* — Clark & Elbing LLP; Karen L. Elbing

(57) ABSTRACT

The vascular endothelial growth factor (VEGF) activity in a patient's bloodstream or other biological sample can serve as a diagnostic and prognostic index for cancer, diabetes, heart conditions, and other pathologies. Antibody-sandwich ELISA methods and kits for VEGF as an antigen are provided to detect types of VEGF levels in biological samples from animal models and human patients and can be used as a diagnostic/prognostic index.

3 Claims, 3 Drawing Sheets

OTHER PUBLICATIONS

Houck et al., "Dual regulation of vascular endothelial growth factor bioavailability by genetic and proteolytic mechanisms" *Journal of Biological Chemistry* 267(36):26031-26037 (Dec. 25, 1992).

Houck et al., "The Vascular Endothelial Growth Factor Family: Identification of a Fourth Molecular Species and Characterization of Alternative Splicing of RNA" *Mol. Endocrinol.* 5(12):1806-14 (1991).

Jingjing et al., "Human M ller cells express VEGF183, a novel spliced variant of vascular endothelial growth factor" *Invest Ophthalmol Vis Sci.* 40(3):752-9 (Mar. 1999).

Keck et al., "Disulfide Structure of the Heparin Binding Domain in Vascular Endothelial Growth Factor: Characterization of Post-translational Modifications in VEGF" *Archives of Biochemistry & Biophysics* 344(1):103-113 (Aug. 1, 1997).

Keyt et al., "Identification of Vascular Endothelial Growth Factor Determinants for Binding KDR and FLT-1 Receptors: Generation of Receptor-Selective VEGF Variants by Site-Directed Mutagenesis" *Journal of Biological Chemistry* 271(10):5638-5646 (Mar. 8, 1996).

Keyt et al., "The Carboxyl-terminal Domain (111-165) of Vascular Endothelial Growth Factor Is Critical for Its Mitogenic Potency" *Journal of Biological Chemistry* 271(13):7788-7795 (Mar. 29, 1996).

Kim et al., "The Vascular Endothelial Growth Factor Proteins: Identification of Biologically Relevant Regions by Neutralizing Monoclonal Antibodies" *Growth Factors* 7:53-64 (1992).

Kohn, E.C., "Angiogenesis in ovarian carcinoma: a formidable biomarker" *Cancer* 80(12):2219-2221 (Dec. 15, 1997).

Kondo et al., "Vascular endothelial growth factor/vascular permeability factor is detectable in the sera of tumor-bearing mice and cancer patients" *Biochimica et Biophysica Acta* 1221:211-214 (1994).

Konecny et al., "Association Between HER-2/neu and Vascular Endothelial Growth Factor Expression Predicts Clinical Outcome in Primary Breast Cancer Patients" *Clinical Cancer Research* 10:1706-1716 (Mar. 1, 2004).

Lee et al., "Processing of VEGF-A by matrix metalloproteinases regulates bioavailability and vascular patterning in tumors" *J Cell Biol.* 169(4):681-91 (May 23, 2005).

Leith and Michelson, "Secretion rates and levels of vascular endothelial growth factor in clone A or HCT-8 human colon tumour cells as a function of oxygen concentration" *Cell Prolif.* 28:415-430 (1995).

Lopez et al., "Transdifferentiated retinal pigment epithelial cells are immunoreactive for vascular endothelial growth factor in surgically excised age-related macular degeneration-related choroidal neovascular membranes" *Invest. Ophthalmol. Vis. Sci.* 37(5):855-868 (Apr. 1996).

Mattern et al., "Association of vascular endothelial growth factor expression with intratumoral microvessel density and tumour cell proliferation in human epidermoid lung carcinoma" *Brit. J. Cancer* 73:931-934 (1996).

Muller et al., "Vascular Endothelial Growth Factor: Crystal Structure and Functional Mapping of the Kinase Domain Receptor Binding Site" *Proc. Natl. Acad. Sci. USA* 94:7192-7197 (Jul. 1997).

Obermair et al., "Concentration of vascular endothelial growth factor (VEGF) in the serum of patients with suspected ovarian cancer" *British Journal of Cancer* 77(11):1870-1874 (1998).

Poltorak et al., "VEGF$_{145}$, a secreted vascular endothelial growth factor isoform that binds to extracellular matrix" *J Biol Chem.* 272(11):7151-8 (Mar. 14, 1997).

Rodriguez et al., "A Sensitive Fluorometric Enzyme-Linked Immunosorbent Assay That Measures Vascular Endothelial Growth Factor$_{165}$ in Human Plasma." *J. Immunol. Methods* 219:45-55 (1998).

Roth et al., "Plasmin modulates vascular endothelial growth factor-A-mediated angiogenesis during wound repair" *Am J Pathol.* 168(2):670-84 (Feb. 2006).

Shifren et al., "Ovarian steroid regulation of vascular endothelial growth factor in the human endometrium: implications for angiogenesis during the menstrual cycle and in the pathogenesis of endometriosis" *J. Clin. Endocrinol. Metab.* 81(8):3112-3118 (1996).

Stimpfl, "Vascular Endothelial Growth Factor Splice Variants and Their Prognostic Value in Breast and Ovarian Cancer" *Clinical Cancer Research* 8:2253-2259 (Jul. 2002).

Takano et al., "Concentration of vascular endothelial growth factor in the serum and tumor tissue of brain tumor patients" *Cancer Research* 56:2185-2190 (May 1, 1996).

Tischer et al., "The human gene for vascular endothelial growth factor. Multiple protein forms are encoded through alternative exon splicing" *Journal of Biological Chemistry* 266(18):11947-11954 (Jun. 25, 1991).

Toi et al., "Quantitative analysis of vascular endothelial growth factor in primary breast cancer" *Cancer* 77(6):1101-1106 (Mar. 15, 1996).

Webb et al., "Vascular Endothelial Growth Factor (VEGF) is Released From Platelets During Blood Clotting: Implications for Measurement of Circulating VEGF Levels in Clinical Disease." *Clinical Science.* 94:395-404 (1998).

Yang et al., "Substantially attenuated hemodynamic responses to *Escherichia coli*-derived vascular endothelial growth factor given by intravenous infusion compared with bolus injection" *J. Pharm. Exp. Ther.* 284(1):103-110 (1998).

Yeo et al., "Development of time-resolved immunofluorometric assay of vascular permeability factor" *Clinical Chemistry* 38(1):71-75 (1992).

Yeo et al., "Vascular permeability factor (vascular endothelial growth factor) in guinea pig and human tumor and inflammatory effusions" *Cancer Research* 53:2912-2918 (Jun. 15, 1993).

Notice of Reasons for Rejection issued for JP 2009-531581 issued on Dec. 13, 2011.

Russian Office Action issued for RU 2009116611/15.

"European Article (4(3) EPC Communication for EP Patent Application No. 07 868 362.0-2404".

Extended European Search Report for European Application No. 11189401.0, dated May 3, 2012.

First Examination Report for New Zealand Patent Application No. 597336, mailed Dec. 23, 2011.

Office Action for Chinese Patent Application No. 200780036803.0, mailed Apr. 19, 2012.

Office Action for European Patent Application No. 07868362.0, mailed Oct. 2, 2012.

Office Action for Russian Patent Application No. 2009116611/15, mailed Aug. 21, 2012.

Office Action and Search Report for Taiwanese Patent Application No. 096137100, mailed Jul. 23, 2012.

Notice of Reasons for Rejection for Japanese Patent Application No. JP 2009-531581, dated Apr. 2, 2013.

\* cited by examiner

ANTI-VEGF ANTIBODIES

RELATED APPLICATION

This application is a continuation of U.S. Ser. No. 11/866,560, filed on Oct. 3, 2007, now abandoned, which claims priority to and the benefit of U.S. Provisional Application No. 60/828,203, filed Oct. 4, 2006, the specification of which is incorporated herein in its entirety.

FIELD OF THE INVENTION

This invention relates to immunoassays for detecting certain populations of VEGF that can be used as diagnostic and prognostic methods for patients with cancer, cardiovascular, or other pathologies.

BACKGROUND

It is now well established that angiogenesis is implicated in the pathogenesis of a variety of disorders. These include solid tumors, intra-ocular neovascular syndromes such as proliferative retinopathies or age-related macular degeneration (AMD), rheumatoid arthritis, and psoriasis (Folkman et al. *J. Biol. Chem.* 267:10931-10934 (1992); Klagsbrun et al. *Annu. Rev. Physiol.* 53:217-239 (1991); and Garner A, *Vascular diseases. In: Pathobiology of ocular disease. A dynamic approach.* Garner A, Klintworth G K, Eds. $2^{nd}$ Edition (Marcel Dekker, NY, 1994), pp 1625-1710). In the case of solid tumors, the neovascularization allows the tumor cells to acquire a growth advantage and proliferative autonomy compared to the normal cells. Accordingly, a correlation has been observed between density of microvessels in tumor sections and patient survival in breast cancer as well as in several other tumors (Weidner et al. *N Engl J Med* 324:1-6 (1991); Horak et al. *Lancet* 340:1120-1124 (1992); and Macchiarini et al. *Lancet* 340:145-146 (1992)).

The search for positive regulators of angiogenesis has yielded many candidates, including, e.g., aFGF, bFGF, TGF-α, TGF-β, HGF, TNF-α, angiogenin, IL-8, etc. (Folkman et al., supra, and Klagsbrun et al., supra). Some of the negative regulators so far identified include thrombospondin (Good et al. *Proc. Natl. Acad. Sci. USA.* 87:6624-6628 (1990)), the 16-kilodalton N-terminal fragment of prolactin (Clapp et al. *Endocrinology,* 133:1292-1299 (1993)), angiostatin (O'Reilly et al. *Cell* 79:315-328 (1994)), and endostatin (O'Reilly et al. *Cell* 88:277-285 (1996)).

Work done over the last several years has established the key role of vascular endothelial growth factor (VEGF) in the regulation of normal and abnormal angiogenesis (Ferrara et al. *Endocr. Rev.* 18:4-25 (1997)). The finding that the loss of even a single VEGF allele results in embryonic lethality points to an irreplaceable role played by this factor in the development and differentiation of the vascular system (Ferrara et al., supra).

Furthermore, VEGF has been shown to be a key mediator of neovascularization associated with tumors and intra-ocular disorders (Ferrara et al., supra). The VEGF mRNA is overexpressed by the majority of human tumors examined (Berkman et al. *J Clin Invest* 91:153-159 (1993); Brown et al. *Human Pathol.* 26:86-91 (1995); Brown et al. *Cancer Res.* 53:4727-4735 (1993); Mattern et al. *Brit. J. Cancer.* 73:931-934 (1996); and Dvorak et al. *Am J. Pathol.* 146:1029-1039 (1995)). Also, the concentration of VEGF in eye fluids is highly correlated to the presence of active proliferation of blood vessels in patients with diabetic and other ischemia-related retinopathies (Aiello et al. *N. Engl. J. Med.* 331:1480-1487 (1994)). Furthermore, studies have demonstrated the localization of VEGF in choroidal neovascular membranes in patients affected by acute macular degeneration (AMD) (Lopez et al. *Invest. Ophtalmo. Vis. Sci.* 37:855-868 (1996)).

VEGF is produced by tissues and does not have to enter the circulation to exert its biological effect, but rather acts locally as a paracrine regulator. A recent study by Yang et al. *J. Pharm. Exp. Ther.* 284:103 (1998) found the clearance of rhVEGF$_{165}$ from the circulation to be very rapid, suggesting endogenous VEGF in the circulation is most likely the result of continual synthesis of VEGF. In addition, several studies have tried to correlate levels of circulating VEGF with tumor burden and have suggested VEGF levels as a potential prognostic marker (Ferrari and Scagliotti *Eur. J. Cancer* 32A:2368 (1996); Gasparini et al. *J. Natl. Cancer Inst.* 89:139 (1997); Kohn *Cancer* 80:2219 (1997); Baccala et al. *Urology* 51:327 (1998); Fujisaki et al. *Am. J. Gastroenterol.* 93:249 (1998)). Clearly the ability to accurately measure VEGF will be important to understand its potential role(s) in many biological processes, such as maintenance of vascular patency, menstrual cycle, ischemia, diabetes, cancer, intraocular disorders, etc.

The literature reports widely varying concentrations of endogenous VEGF in normal and diseased patients, ranging from undetectable to high levels. The ability to measure endogenous VEGF levels depends on the availability of sensitive and specific assays. Colorimetric, chemiluminescence, and fluorometric based enzyme-linked immunosorbent assays (ELISAs) for VEGF have been reported. Houck et al., supra, (1992); Yeo et al. *Clin. Chem.* 38:71 (1992); Kondo et al. *Biochim. Biophys. Acta* 1221:211 (1994); Baker et al. *Obstet. Gynecol.* 86:815 (1995); Hanatani et al. *Biosci. Biotechnol. Biochem.* 59:1958 (1995); Leith and Michelson *Cell Prolif.* 28:415 (1995); Shifren et al. *J. Clin. Endocrinol. Metab.* 81:3112 (1996); Takano et al. *Cancer Res.* 56:2185 (1996); Toi et al. *Cancer* 77:1101 (1996); Brekken et al. *Cancer Res.* 58:1952 (1998); Obermair et al. *Br. J. Cancer* 77:1870-1874 (1998); Webb et al. *Clin. Sci.* 94:395-404 (1998).

For example, Houck et al., supra (1992) describe a colorimetric ELISA that appears to have ng/ml sensitivity, which may not be sensitive enough to detect endogenous VEGF levels. Yeo et al., supra (1992) describe a two-site time-resolved immunofluorometric assay, however, no VEGF was detected in normal sera (Yeo et al. *Cancer Res.* 53:2912 (1993)). Baker et al., supra (1995), using a modified version of this immunofluorometric assay, reported detectable levels of VEGF in plasma from pregnant women, with higher levels observed in women with preeclampsia. Similar data in pregnant women were reported by Anthony et al. *Ann. Clin. Biochem.* 34:276 (1997) using a radioimmunoassay. Hanatani et al., supra (1995) developed a chemiluminescent ELISA capable of measuring circulating VEGF and report VEGF levels in sera from 30 normal individuals (male and female) from 8-36 pg/ml. Brekken et al, supra (1998) described ELISA assays using antibodies having binding preference to either the VEGF alone or the VEGF:Flk-1 complex.

An ELISA kit for VEGF detection is commercially available from R&D Systems (Minneapolis, Minn.). The R&D VEGF ELISA kit has been used in sandwich assays wherein a monoclonal antibody is used to capture the target VEGF antigen and a polyclonal antibody is used to detect the VEGF. Webb et al. supra (1998). See, also, e.g., Obermair et al., supra (1998).

Keyt et al. *J. Biol. Chem.* 271:7788-7795 (1996); Keyt et al. *J. Biol. Chem.* 271:5638 (1996); and Shifren et al., supra (1996) also developed a colorimetric ELISA based on a dual monoclonal antibody pair. Although this ELISA was able to detect elevated VEGF levels in cancer patients, it lacked the sensitivity needed to measure endogenous levels of VEGF in normal individuals. Rodriguez et al. *J. Immunol. Methods* 219:45 (1998) described a two-site fluorimetric VEGF ELISA that yields a sensitivity of 10 pg/ml VEGF in neat plasma or serum. However, this fluorimetric assay detects fully intact 165/165 and 165/110 species of VEGF (It has been reported that VEGF 165/165 can be proteolytically cleaved into three other forms: a 165/110 heterodimer, a 110/110 homodimer, and a 55-amino-acid C-terminal fragment (Keyt et al. *J. Biol. Chem.* 271:7788-7795 (1996); Keck et al. *Arch. Biochem. Biophys.* 344:103-113 (1997)).).

Thus, there is a need to develop a diagnostic and prognostic assay that detects higher measurable levels of VEGF in a biological sample of an animal model or patient than existing ELISAs, and/or can measure different isoforms of VEGF.

SUMMARY

Antibody-sandwich ELISA methods for VEGF as an antigen were developed to detect VEGF forms in biological samples. The VEGF ELISA provided herein is capable of detecting VEGF isoforms and fragments of VEGF greater than 110 ("$VEGF_{110+}$"). Kits thereof are also provided.

For example, methods for detecting selective vascular endothelial growth factor (VEGF) forms greater than 110 amino acids ($VEGF_{110+}$) in a biological sample comprise the steps of: (a) contacting and incubating the biological sample with a capture reagent immobilized to a solid support, wherein the capture reagent is an antibody that recognizes same epitope as antibody 5C3 against human VEGF, said monoclonal antibody binding specifically to residues greater than 110 of human VEGF; (b) separating the biological sample from the immobilized capture reagents; (c) contacting the immobilized capture reagent-target molecule complex with a detectable antibody that binds to the KDR and/or FLT1 receptor binding domains of VEGF; and (d) measuring the level of $VEGF_{110+}$ bound to the capture reagents using a detection means for the detectable antibody. In certain embodiments, the detectable antibody binds to an epitope in VEGF 1-110. In certain embodiments, comparison ELISA can be performed to detect different types of VEGF. In certain embodiments, the biological sample (e.g., tumor samples or tumor lysates, plasma, serum, or urine, etc.) is isolated from a human subject.

In one embodiment, the capture reagent is the 5C3 monoclonal antibody. In one embodiment, the immobilized capture reagent is coated on a microtiter plate. In certain embodiments, the detectable antibody is a monoclonal antibody. In one embodiment, the detectable antibody is a murine monoclonal antibody. In one embodiment, the immobilized monoclonal antibody is MAb 5C3 and the detectable antibody is MAb A4.6.1. In certain embodiments, the detectable antibody is directly detectable. In one embodiment, detectable antibody is amplified by a colorimetric reagent. In one embodiment, the detectable antibody is biotinylated and the detection means is avidin or streptavidin-peroxidase and 3,3', 5,5'-tetramethyl benzidine.

In certain embodiments of the invention, the human subject is a vascular, diabetic, or cancer patient and the measuring step (d) further comprises a comparison with a standard curve to determine the level of VEGF compared to a normal individual.

Kits are also provided. For example, an immunoassay kit for detecting vascular endothelial growth factor (VEGF) forms greater than 110 amino acids ($VEGF_{110+}$) in a biological sample can comprise: (a) as capture reagent, an antibody against human VEGF, wherein the monoclonal antibody binds specifically to the residues greater than 110 of human VEGF; and (b) as detection reagent, a detectable antibody that binds to the KDR and/or FLT1 receptor binding domains of VEGF. In certain embodiments, the detectable antibody binds to an epitope in VEGF 1-110. In certain embodiments, the kit, further comprises a solid support for the capture reagents. For example, the capture reagents can be immobilized on the solid support (e.g., a microtiter plate). In certain embodiments, the kit further comprises a detection means (e.g., colormetric means, fluorimetric means, etc.) for the detectable antibodies. In certain embodiments, the kit further comprises purified VEGF as an antigen standard. In certain embodiments of the invention, an additional VEGF ELISA or more can be provided for comparison studies with the $VEGF_{110+}$ ELISA. In one embodiment, the kit includes a capture reagent monoclonal antibody, which is murine monoclonal antibody MAb 5C3, and a detectable antibody, which is MAb A4.6.1.

In yet another embodiment, the invention provides an anti-VEGF antibody 5C3 (obtainable from or produced by hybridoma deposited under ATCC number PTA-7737). The invention also provides an antibody that does not bind VEGF 1-110 and binds to the same $VEGF_{110+}$ epitope as the monoclonal antibody produced by hybridoma cell line PTA-7737. In certain embodiments, an antibody of the invention is conjugated to a detectable label. In one embodiment, the hybridoma 5C3.1.1 deposited under ATCC deposit number PTA-7737 is provided.

DETAILED DESCRIPTION

Definitions

Before describing the present invention in detail, it is to be understood that this invention is not limited to particular compositions or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a molecule" optionally includes a combination of two or more such molecules, and the like.

Figure 1A:
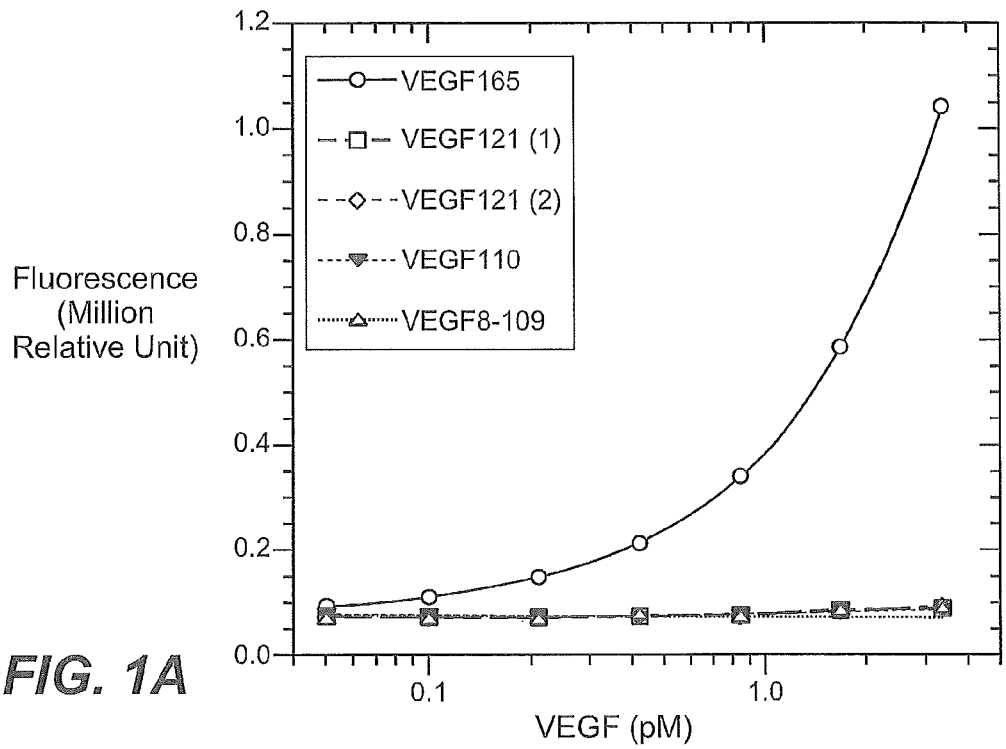
FIG. 1, Panels A, B and C illustrates the detection of recombinant VEGF165, VEGF121(1) (truncated, likely missing approximately 9 amino acids from the carboxy-terminus according to the manufacturer, R&D systems), VEGF121 (2) (from Pepro Tech), VEGF110 (N-terminal fragment generated by plasmin digestion of VEGF) and VEGF8-109 (artificial VEGF with amino acids 8-109 of VEGF165) molecules by different VEGF ELISAs. (A). ELISA A using 3.5F8 for coat and biotinylated A4.6.1 for detection. (B). ELISA B using A4.6.1 for coat and biotinylate 2E3 for detection. (C). ELISA C using 5C3 for coat and biotinylated A4.6.1 for detection.

The term "VEGF" as used herein refers to the 165-amino acid vascular endothelial cell growth factor, and related 121-, 145-, 189-, and 206-amino acid vascular endothelial cell growth factors, as described by Leung et al. *Science* 246:1306 (1989), Houck et al. *Mol. Endocrin.* 5:1806 (1991), and Neufeld et al., supra, together with the naturally occurring allelic and processed forms of those growth factors. See also, e.g., FIGS. 1A and B of U.S. Pat. No. 6,057,428. Active VEGF fragment can be released from ECM-bound VEGF by plasmin cleavage, generating the first 110 amino acids (see, e.g., Keyt B A, et al.: *The carboxyl-terminal domain (111-165) of vascular endothelial growth factor is critical for its mitogenic potency. J Biol. Chem.* 271: 7788-7795 (1996)). "$VEGF_{110+}$" as used herein refers to VEGF fragments that are greater than 110 amino acids (from the N-terminal), but do not include the first 110 amino acids or smaller fragments (e.g., $VEGF_{8-109}$).

The term "detecting" is used in the broadest sense to include both qualitative and quantitative measurements of a target molecule. In one aspect, the detecting method as described herein is used to identify the mere presence of $VEGF_{110+}$ or VEGF in a biological sample. In another aspect, the method is used to test whether $VEGF_{110+}$ or VEGF in a sample is at a detectable level. In yet another aspect, the method can be used to quantify the amount of $VEGF_{110+}$ or VEGF in a sample and further to compare the $VEGF_{110+}$ or VEGF levels from different samples.

The term "biological sample" refers to a body sample from any animal, but preferably is from a mammal, more preferably from a human. In certain embodiments, such biological sample is from a vascular, diabetic, or cancer patient. Such samples include biological fluids such as serum, plasma, vitreous fluid, lymph fluid, synovial fluid, follicular fluid, seminal fluid, amniotic fluid, milk, whole blood, urine, cerebrospinal fluid, saliva, sputum, tears, perspiration, mucus, tumor lysates, and tissue culture medium, as well as tissue extracts such as homogenized tissue, tumor tissue, and cellular extracts. In certain embodiments, the sample is a body sample from any animal, in one embodiment it is from a mammal, in one embodiment from a human subject. In one embodiment, such biological sample is from clinical patients.

The term "detectable antibody" refers to an antibody that is capable of being detected either directly through a label amplified by a detection means, or indirectly through, e.g., another antibody that is labeled. For direct labeling, the antibody is typically conjugated to a moiety that is detectable by some means. In one embodiment, the detectable antibody is biotinylated antibody.

The term "detection means" refers to a moiety or technique used to detect the presence of the detectable antibody in the ELISA herein and includes detection agents that amplify the immobilized label such as label captured onto a microtiter plate. In one embodiment, the detection means is a colorimetric detection agent such as avidin or streptavidin-HRP.

The term "capture reagent" refers to a reagent capable of binding and capturing a target molecule in a sample such that under suitable condition, the capture reagent-target molecule complex can be separated from the rest of the sample. Typically, the capture reagent is immobilized or immobilizable. In a sandwich immunoassay, the capture reagent is preferably an antibody or a mixture of different antibodies against a target antigen.

The term "antibody" herein is used in the broadest sense and specifically covers intact monoclonal antibodies, polyclonal antibodies, multispecific antibodies (e.g. bispecific antibodies) formed from at least two intact antibodies, and antibody fragments so long as they exhibit the desired biological activity.

"Antibody fragments" comprise a portion of an intact antibody, preferably comprising the antigen-binding or variable region thereof. Examples of antibody fragments include Fab, Fab', F(ab')$_2$, and Fv fragments; diabodies; linear antibodies; single-chain antibody molecules; and multispecific antibodies formed from antibody fragments.

For the purposes herein, an "intact antibody" is one comprising heavy- and light-chain variable domains as well as an Fc region.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light-chain and heavy-chain variable domains.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature,* 256:495 (1975), or may be made by recombinant DNA methods (see, e.g., U.S. Pat. No. 4,816,567). The "monoclonal antibodies" may also be isolated from phage antibody libraries using the techniques described in Clackson et al. *Nature* 352:624-628 (1991) and Marks et al., *J. Mol. Biol.,* 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA,* 81:6851-6855 (1984)). Chimeric antibodies of interest herein include "primatized" antibodies comprising variable-domain antigen-binding sequences derived from a non-human primate (e.g. Old World Monkey, such as baboon, rhesus or cynomolgus monkey) and human constant-region sequences (U.S. Pat. No. 5,693,780).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made further to refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature,* 321:522-525 (1986); Riechmann et al., *Nature,* 332:323-329 (1988); and Presta, *Curr. Op. Struct. Biol.,* 2:593-596 (1992). In one embodiment, a humanized 5C3 antibody is provided and used the methods provided herein.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions in both the light-chain and the heavy-chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest, 5th Ed. Public Health Service*, National Institutes of Health, Bethesda; Md. (1991)). The constant domains are not involved directly in binding an antibody to an antigen, but exhibit various effector functions, such as participation of the antibody in antibody-dependent cellular cytotoxicity (ADCC).

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-binding sites and is still capable of cross-linking antigen.

"Fv" is the minimum antibody fragment that contains a complete antigen-recognition and antigen-binding site. This region consists of a dimer of one heavy-chain and one light-chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy-chain CH1 domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments that have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of antibodies are called α, δ, ε, γ and μ, respectively. The subunit structures and three-dimensional configurations of different classes of immunoglobulins are well known.

"Single-chain Fv" or "scFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains that enables the scFv to form the desired structure for antigen binding. For a review of scFv, see Pluckthun in *The Pharmacology of Monoclonal Antibodies*, vol. 113, Rosenburg and Moore eds., Springer-Verlag, New York, pp. 269-315 (1994).

The term "hypervariable region" when used herein refers to the amino acid residues of an antibody that are responsible for antigen binding. The hypervariable region comprises amino acid residues from a "complementarity-determining region" or "CDR" (e.g. residues 24-34 (L1), 50-56 (L2) and 89-97 (L3) in the light-chain variable domain and 31-35 (H1), 50-65 (H2) and 95-102 (H3) in the heavy-chain variable domain; Kabat et al., *Sequences of Proteins of Immunological Interest, 5th Ed. Public Health Service*, National Institutes of Health, Bethesda, Md. (1991)) and/or those residues from a "hypervariable loop" (e.g. residues 26-32 (L1), 50-52 (L2) and 91-96 (L3) in the light-chain variable domain and 26-32 (H1), 53-55 (H2) and 96-101 (H3) in the heavy-chain variable domain; Chothia and Lesk *J. Mol. Biol.* 196:901-917 (1987)). "Framework" or "FR" residues are those variable domain residues other than the hypervariable region residues as herein defined.

"Mammal" for purposes of treatment refers to any animal classified as a mammal, including humans, domestic, and farm animals, and zoo, sports, or pet animals, such as dogs, horses, cats, sheep, pigs, cows, etc. Preferably, the mammal is human.

The terms "cancer", "cancerous", and "malignant" refer to or describe the physiological condition in mammals that is typically characterized by unregulated cell growth. Examples of cancer include but are not limited to, carcinoma including adenocarcinoma, lymphoma, blastoma, melanoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), gastrointestinal stromal cancer, pancreatic cancer, glioblastoma, cervical cancer, ovarian cancer, liver cancer (e.g., hepatic carcinoma and hepatoma), bladder cancer, hepatoma, breast cancer, colon cancer, colorectal cancer, rectal cancer, endometrial or uterine carcinoma, salivary gland carcinoma, kidney or renal cancer, liver cancer, prostate cancer, vulval cancer, thyroid cancer, basal cell carcinoma, testicular cancer, esophageal cancer, hepatic carcinoma, soft-tissue sarcoma, kaposi's sarcoma, carcinoid carcinoma, mesothelioma, multiple myeloma, and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); Hodgkin's lymphoma, chronic lymphocytic leukemia (CLL), acute lymphoblastic leukemia (ALL), Hairy cell leukemia; chronic myeloblastic leukemia, and post-transplant lymphoproliferative disorder (PTLD), as well as abnormal vascular proliferation associated with phakomatoses, edema (such as that associated with brain tumors), and Meigs' syndrome.

The phrases "vascular" and "cardiovascular" are used interchangeably and describe patients with indications that stimulate angiogenesis and/or cardiovascularization, and those that inhibit angiogenesis and/or cardiovascularization. Such disorders include, for example, arterial disease, such as atherosclerosis, hypertension, inflammatory vasculitis, Reynaud's disease and Reynaud's phenomenon, aneurysms, and arterial restenosis; venous and lymphatic disorders such as thrombophlebitis, lymphangitis, and lymphedema; and other vascular disorders such as peripheral vascular disease, AMD, cancer such as vascular tumors, e.g., hemangioma (capillary and cavernous), glomus tumors, telangiectasia, bacillary angiomatosis, hemangioendothelioma, angiosarcoma, hemangiopericytoma, Kaposi's sarcoma, lymphangioma, and lymphangiosarcoma, tumor angiogenesis, trauma such as wounds, burns, and other injured tissue, implant fixation, scarring, ischemia reperfusion injury, rheumatoid arthritis, cerebrovascular disease, renal diseases such as acute renal failure, and osteoporosis. This would also include angina, myocardial infarctions such as acute myocardial infarctions, cardiac hypertrophy, and heart failure such as congestive heart failure (CHF).

The term "diabetes" refers to a progressive disease of carbohydrate metabolism involving inadequate production or utilization of insulin and is characterized by hyperglycemia and glycosuria. This term includes all forms of diabetes, such as type I and type II diabetes and insulin-resistant diabetes, such as Mendenhall's Syndrome, Werner Syndrome, leprechaunism, lipoatrophic diabetes, and other lipoatrophies.

The term "affinity purified" refers to purifying a substance by eluting it through an affinity chromatography column. ELISA Vascular endothelial growth factor (VEGF) is a homodimeric glycoprotein and is a key angiogenic factor of blood vessel formation during development and in pathological angiogenesis associated with tumors. Expression of VEGF is potentiated in response to hypoxia, and potentially other factors such as growth factors, hormones and oncogenes. (see, e.g., Ferrara N: *Vascular endothelial growth factor: Basic science and clinical progress. Endocrine Reviews* 25: 581-611 (2004)). The human VEGF gene has eight exons separated by introns. Alternative RNA splicing results in the generation of at least four major isoforms having 121, 165, 189 and 206 amino acids in monomer (see, e.g., Houck K A, et al.: *The vascular endothelial growth factor family: identification of a fourth molecular species and characterization of alternative splicing of RNA. Mol Endocrinol* 5: 1806-1814 (1991); and, Tischer E, et al.: *The human gene for vascular endothelial growth factor. Multiple protein forms are encoded through alternative exon splicing. J Biol Chem* 266: 11947-11954 (1991)). Less frequent isoforms including those having 145 (see, e.g., Poltorak Z., et al.: *VEGF145, a secreted vascular endothelial growth factor isoform that binds to extracellular matrix. J Biol Chem* 272: 7151-7158 (1997)) and 183 (see, e.g., Jingjing L, et al.: *Human Muller cells express VEGF183, a novel spliced variant of vascular endothelial growth factor. Invest Opthalmol V is Sci* 40:752-759 (1999)) amino acids in monomer have also been reported. All VEGF isoforms bind two receptor tyrosine kinases, VEGFR-1 (see, e.g., De Vries C, et al.: *The fms-like tyrosine kinase, a receptor for vascular endothelial growth factor. Science* 255:989-991 (1992)) and VEGFR-2 (see, e.g., Terman B I, et al.: *Identification of a new endothelial cell growth factor receptor tyrosine kinase. Oncogene* 6:1677-1683 (1991)). VEGF$_{165}$ also interacts with neuropilin (see, e.g., Soker S. et al.: *Neuropilin-1 is expressed by endothelial and tumor cells as an isoform-specific receptor for vascular endothelial growth factor. Cell* 92: 735-745 (1998)). VEGF$_{189}$ and VEGF$_{206}$ bind to heparin with a high affinity and are mostly sequestered in the extracellular matrix (ECM). VEGF$_{165}$ binds to heparin with intermediate affinity and is partially soluble and partially bound to cell surface and ECM. VEGF$_{121}$ does not bind to heparin and is freely soluble. VEGF$_{121}$ and VEGF$_{165}$ were found to be the most dominantly expressed variants in breast and ovarian cancer tumor specimens and cell lines by reverse transcription-PCR analysis, while VEGF$_{206}$ expression was not detected. VEGF$_{183}$ and VEG$_{189}$ expression was found to be non-detectable or at low levels in the cell lines and were detected in some of the tumor specimens (see, e.g., Stimpfl M, et al.: *Vascular Endothelial growth factor splice variants and their prognostic value in breast and ovarian cancer. Clinical Cancer Research* 8: 2253-2259 (2002)).

Active VEGF fragment can be released from ECM-bound VEGF by plasmin cleavage, generating the first 110 amino acids (see, e.g., Keyt B A, et al., *The carboxyl-terminal domain* (111-165) *of vascular endothelial growth factor is critical for its mitogenic potency. J Biol. Chem.* 271: 7788-7795 (1996)). This could be a mechanism to locally regulate the bioavailability of VEGF during physiological and pathological processes of angiogenesis. See, e.g., Houck K A, et al. *Dual regulation of vascular endothelial growth factor bioavailability by genetic and proteolytic mechanisms. J Biol Chem* 1992; 267:26031-26037 (1992); Keyt B A, et al. *The carboxy-terminal domain* (111-165) *of vascular endothelial growth factor is critical for its mitogenic potency. J Biol. Chem.* 271:7788-7795 (1996); and, Roth D, et al. *Plasmin modulates vascular endothelial growth factor-A-mediated angiogenesis during wound repair. Am Pathology* 168: 670-684. (10-12) (2006). However, VEGF$_{110}$ concentrations in biological samples have not been reported. Active VEGF fragments may also be released from ECM-bound VEGF by matrix metalloproteinase (MMP) cleavage. This is supported by the finding of degraded VEGF fragments with amino acids additional to 1-110 in ascites from ovarian cancer patients. Both plasmin and MMP3 were detected in the ascites. See, e.g., Lee S, Shahla M J, et al. *Processing of VEGF-A by matrix metalloproteinases regulates bioavailability and vascular patterning in tumors. J Cell Biology* 169:681-691 (2005).

Enzyme-linked immunosorbent assays (ELISAs) for various antigens include those based on colorimetry, chemiluminescence, and fluorometry. ELISAs have been successfully applied in the determination of low amounts of drugs and other antigenic components in plasma and urine samples, involve no extraction steps, and are simple to carry out. The assay described herein is an ELISA that utilizes antibodies as capture reagents and detectable antibodies for VEGF and $VEGF_{110+}$. In certain embodiments, the ELISA is cell-based. In the first step of the assay the biological sample suspected of containing VEGF or containing $VEGF_{110+}$ is contacted and incubated with the capture (or coat) antibodies so that the capture antibodies capture or bind to the VEGF or $VEGF_{110+}$ so that it can be detected in a detection step. The detection step involves use of the detectable antibody, which, when contacted with any of the bound VEGF or $VEGF_{110+}$, binds to the protein of interest, if present, and a detection means is used to detect the label on the antibody and hence the presence or amount of VEGF or $VEGF_{110+}$ present. This ELISA can be compared with an ELISA that recognizes total VEGF (e.g., U.S. Pat. No. 6,855,508; those described herein, and those known in the art) or isoforms of VEGF to determine the type of VEGF present.

For example, in certain embodiments, the assay utilizes the following steps.

First Step

In the first step of the assay herein, the biological sample is contacted and incubated with the immobilized capture (or coat) reagent, which is an anti-VEGF monoclonal antibody. This antibody may be from any species, but preferably the monoclonal antibody is a murine or rat monoclonal antibody, more preferably murine, and most preferably MAb 5C3 derived from the hybridoma identified herein. Hence, in a specific preferred embodiment, the immobilized monoclonal antibody is a murine monoclonal antibody, most preferably MAb 5C3. Immobilization conventionally is accomplished by insolubilizing the capture reagent either before the assay procedure, as by adsorption to a water-insoluble matrix or surface (U.S. Pat. No. 3,720,760) or non-covalent or covalent coupling (for example, using glutaraldehyde or carbodiimide cross-linking, with or without prior activation of the support with, e.g., nitric acid and a reducing agent as described in U.S. Pat. No. 3,645,852 or in Rotmans et al. *J. Immunol. Methods* 57:87-98 (1983)), or afterward, e.g., by immunoprecipitation.

The solid phase used for immobilization may be any inert support or carrier that is essentially water insoluble and useful in immunometric assays, including supports in the form of, e.g., surfaces, particles, porous matrices, etc. Examples of commonly used supports include small sheets, Sephadex, polyvinyl chloride, plastic beads, and assay plates or test tubes manufactured from polyethylene, polypropylene, polystyrene, and the like including 96-well microtiter plates, as well as particulate materials such as filter paper, agarose, cross-linked dextran, and other polysaccharides. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are suitably employed for capture reagent immobilization. In one embodiment the immobilized capture reagent is coated on a microtiter plate, and in particular the preferred solid phase used is a multi-well microtiter plate that can be used to analyze several samples at one time, e.g., a microtest 96-well ELISA plate such as that sold as Nune Maxisorb or Immulon. In certain embodiments, the plate is a MICROTEST™ or MAXISORP™ 96-well ELISA plate such as that sold as NUNC MAXISORB™ or IMMULON™.

The solid phase is coated with the capture reagent as defined above, which may be linked by a non-covalent or covalent interaction or physical linkage as desired. Techniques for attachment include those described in U.S. Pat. No. 4,376,110 and the references cited therein. If covalent, the plate or other solid phase is incubated with a cross-linking agent together with the capture reagent under conditions well known in the art, e.g., such as for 1 hour at room temperature.

Commonly used cross-linking agents for attaching the capture reagent to the solid phase substrate include, e.g., 1,1-bis (diazoacetyl)-2-phenylethane, glutaraldehyde, N-hydroxysuccinimide esters, for example, esters with 4-azido-salicylic acid, homobifunctional imidoesters, including disuccinimidyl esters such as 3,3'-dithiobis-(succinimidyl-propionate), and bifunctional maleimides such as bis-N-maleimido-1,8-octane. Derivatizing agents such as methyl-3-[(p-azidophenyl)-dithio]pro-pioimi-date yield photoactivatable intermediates capable of forming cross-links in the presence of light.

If 96-well plates are utilized, they are typically coated with the capture reagent (typically diluted in a buffer such as 0.05 M sodium carbonate by incubation for at least about 10 hours, more preferably at least overnight, at temperatures of about 4-20° C., or about 4-8° C., and at a pH of about 8-12, or about pH 9-10, or about pH 9.6). If shorter coating times are desired, one can coat, e.g., 96-well plates at room temperature for two hours. The plates may be stacked and coated long in advance of the assay itself, and then the assay can be carried out simultaneously on several samples in a manual, semi-automatic, or automatic fashion, such as by using robotics.

The coated plates are then typically treated with a blocking agent that binds non-specifically to and saturates the binding sites to prevent unwanted binding of the free ligand to the excess sites on the wells of the plate. Examples of appropriate blocking agents for this purpose include, e.g., gelatin, bovine serum albumin, egg albumin, casein, and non-fat milk. The blocking treatment typically takes place under conditions of ambient temperatures for about 1-4 hours, preferably about 1 to 3 hours, or overnight at 0-4° C.

After coating and blocking, the VEGF standard (purified VEGF) or the biological sample to be analyzed, appropriately diluted, is added to the immobilized phase. The preferred dilution rate is about 1-15%, preferably about 10%, by volume. Buffers that may be used for dilution for this purpose include (a) PBS containing 0.5% BSA, 0.05% TWEEN 20™ detergent (P20), 0.05% PROCLIN™ 300 antibiotic, 5 mM EDTA, 0.25% Chaps surfactant, 0.2% beta-gamma globulin, and 0.35M NaCl, pH 7.4; (b) PBS containing 0.5% bovine serum albumin, 0.05% polysorbate 20, 5 mM EDTA, 0.25% CHAPS, 0.2% bovine γ-globulins, and 0.35 M NaCl; pH 7.4 (c) PBS containing 0.5% BSA, 0.05% polysorbate 20 (P20), and 0.05% PROCLIN™ 300, pH 7; (d) PBS containing 0.5% BSA, 0.05% P20, 0.05% PROCLIN™ 300, 5 mM EDTA, and 0.35 M NaCl, pH 6.35; (e) PBS containing 0.5% BSA, 0.05% P20, 0.05% PROCLIN™ 300, 5 mM EDTA, 0.2% beta-gamma globulin, and 0.35 M NaCl, pH 7.4; and (f) PBS containing 0.5% BSA, 0.05% P20, 0.05% PROCLIN™ 300, 5 mM EDTA, 0.25% Chaps, and 0.35 M NaCl, pH 7.4. PROCLIN™ 300 acts as a preservative, and TWEEN 20™ acts as a detergent to eliminate non-specific binding.

While the concentration of the capture reagents will generally be determined by the concentration range of interest of the VEGF taking any necessary dilution of the biological sample into account, the final concentration of the capture reagent will normally be determined empirically to maximize the sensitivity of the assay over the range of interest.

The conditions for incubation of sample and immobilized capture reagent are selected to maximize sensitivity of the assay and to minimize dissociation. Preferably, the incubation is accomplished at fairly constant temperatures, ranging from about 0° C. to about 40° C., preferably from about 20 to 25° C. The time for incubation depends primarily on the temperature, being generally no greater than about 10 hours to avoid an insensitive assay. Preferably, the incubation time is from about 0.5 to 3 hours, and more preferably 1.5-3 hours at room temperature to maximize binding of free $VEGF_{110+}$ or VEGF to capture reagents. The duration of incubation may be longer if a protease inhibitor is added to prevent proteases in the biological fluid from degrading the VEGF.

At this stage, the pH of the incubation mixture will ordinarily be in the range of about 4-9.5, preferably in the range of about 6-9, more preferably about 7-8, and most preferably the pH of the assay (ELISA) diluent is pH 7.4. The pH of the incubation buffer is chosen to maintain a significant level of specific binding of the capture reagent to the $VEGF_{110+}$ or VEGF being captured. Various buffers may be employed to achieve and maintain the desired pH during this step, including borate, phosphate, carbonate, Tris-HCl or Tris-phosphate, acetate, barbital, and the like. The particular buffer employed is not critical to the invention, but in individual assays one buffer may be preferred over another.

Second Step

In the second step of the assay method herein, which is optional, the biological sample is separated (preferably by washing) from the immobilized capture reagent to remove uncaptured molecules. The solution used for washing is generally a buffer ("washing buffer") with a pH determined using the considerations and buffers described above for the incubation step, with a preferable pH range of about 6-9. The washing may be done three or more times. The temperature of washing is generally from refrigerator to moderate temperatures, with a constant temperature maintained during the assay period, typically from about 0-40° C., more preferably about 4-30° C. For example, the wash buffer can be placed in ice at 4° C. in a reservoir before the washing, and a plate washer can be utilized for this step. A cross-linking agent or other suitable agent may also be added at this stage to allow the now-bound $VEGF_{110+}$ or VEGF to be covalently attached to the capture reagent if there is any concern that the captured $VEGF_{110+}$ or VEGF may dissociate to some extent in the subsequent steps.

Third Step

In the next step, the immobilized capture reagent is contacted with detectable antibodies, preferably at a temperature of about 20-40° C., more preferably about 20-25° C., with the exact temperature and time for contacting the two being dependent primarily on the detection means employed. For example, when streptavidin-peroxidase and 3,3',5,5'-tetramethyl benzidine are used as the means for detection, e.g., in one embodiment, the contacting is carried out (e.g., about 1 hour or more) to amplify the signal to the maximum. Preferably a molar excess of an antibody with respect to the maximum concentration of free $VEGF_{110+}$ or VEGF expected (as described above) is added to the plate after it is washed. This antibody is directly or indirectly detectable. While the detectable antibody may be a polyclonal or monoclonal antibody, e.g., in certain embodiments, it is a monoclonal antibody, in one embodiment murine, and in one embodiment MAb A4.6.1. Also, the detectable antibody can be directly detectable, and in one embodiment has a colorimetric label, and in another embodiment has a fluorometric label. More preferably, the detectable antibody is biotinylated and the detection means is avidin or streptavidin-peroxidase and 3,3',5,5'-tetramethyl benzidine. The readout of the detection means can be fluorimetric or colorimetric. The affinity of the antibody must be sufficiently high that small amounts of the free $VEGF_{110+}$ or VEGF can be detected, but not so high that it causes the $VEGF_{110+}$ or VEGF to be pulled from the capture reagents.

Fourth Step

In the last step of the assay method, the level of free VEGF that is now bound to the capture reagent is measured using a detection means for the detectable antibody. If the biological sample is from a vascular, diabetic, or cancer patient, the measuring step preferably comprises comparing the reaction that occurs as a result of the above three steps with a standard curve to determine the level of $VEGF_{110+}$ or VEGF compared to a normal individual, or preferably comprises comparing the reaction that occurs as a result of the above three steps with an another VEGF ELISA recognizing different isoforms or total VEGF to determine the level of the types of VEGF when the ELISAs are compared, and optionally compared to a normal individual.

Antibody Production

Polyclonal antibodies to the VEGF generally are raised in animals by multiple subcutaneous (sc) or intraperitoneal (ip) injections of the VEGF and an adjuvant. It may be useful to conjugate the VEGF or a fragment containing the target amino acid sequence to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, SOCl2, or R1N=C=NR, where R and R1 are different alkyl groups.

The antibodies used as the coat or detectable antibodies may be obtained from any convenient vertebrate source, such as murine, primate, lagomorpha, goat, rabbit, rat, chicken, bovine, ovine, equine, canine, feline, or porcine. Chimeric or humanized antibodies may also be employed, as described, e.g., in U.S. Pat. No. 4,816,567; Morrison et al. *Proc. Natl. Acad. Sci. USA* 81:6851 (1984); Neuberger et al. *Nature* 312: 604 (1984); Takeda et al. *Nature* 314:452 (1985); and WO 98/45331 published Oct. 15, 1998, as well as in those additional references set forth above.

Animals may be immunized against the immunogenic conjugates or derivatives by combining 1 mg or 1 μg of conjugate (for rabbits or mice, respectively) with 3 volumes of Freund's complete adjuvant and injecting the solution intradermally at multiple sites. One month later the animals are boosted with ⅕ to ⅟₁₀ the original amount of conjugate in Freund's incomplete adjuvant by subcutaneous injection at multiple sites. 7 to 14 days later animals are bled and the serum is assayed for anti-VEGF titer. Animals are boosted until the titer plateaus. Preferably, the animal is boosted with the conjugate of VEGF, but conjugated to a different protein and/or through a different cross-linking agent. Conjugates also can be made in recombinant cell culture as protein fusions. Also, aggregating agents such as alum are used to enhance the immune response. Methods for the production of polyclonal antibodies are described in numerous immunology textbooks, such as Davis et al. *Microbiology*, 3$^{rd}$ *Edition*, (Harper & Row, New York, N.Y., 1980).

Monoclonal antibodies are prepared by recovering spleen cells from immunized animals and immortalizing the cells in conventional fashion, e.g. by fusion with myeloma cells or by Epstein-Barr virus transformation, and screening for clones expressing the desired antibody. See, e.g., Kohler and Milstein *Eur. J. Immunol.* 6:511 (1976). Monoclonal antibodies, or the antigen-binding region of a monoclonal antibody, such as Fab or (Fab)$_2$ fragments, may alternatively be produced by recombinant methods.

Examples of suitable antibodies include those already utilized in known RIAs for the protein in question, e.g., those antibodies directed against VEGF as described in the references given in the introduction herein.

In certain embodiments, an anti-VEGF antibody 5C3, which is obtainable from or produced by hybridoma deposited under ATCC number PTA-7737, is used, optionally with another anti-VEGF antibody, A4.6.1. The invention also provides an antibody that does not bind VEGF 1-110 and binds to the same VEGF$_{110+}$ epitope as the monoclonal antibody produced by hybridoma cell line PTA-7737. A hybridoma 5C3.1.1 deposited under ATCC deposit number PTA-7737 is provided.

Detection

The antibody added to the immobilized capture reagents will be either directly labeled, or detected indirectly by addition, after washing off of excess first antibody, of a molar excess of a second, labeled antibody directed against IgG of the animal species of the first antibody. In the latter, indirect assay, labeled antisera against the first antibody are added to the sample so as to produce the labeled antibody in situ.

The label used for either the first or second antibody is any detectable functionality that does not interfere with the binding of free VEGF$_{110+}$ or VEGF to the antibody. Examples of suitable labels are those numerous labels known for use in immunoassay, including moieties that may be detected directly, such as fluorochrome, chemiluminescent, and radioactive labels, as well as moieties, such as enzymes, that must be reacted or derivatized to be detected. Examples of such labels include the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luciferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, biotin/streptavidin, biotin/Streptavidin-β-galactosidase with MUG, spin labels, bacteriophage labels, stable free radicals, and the like. As noted above, the fluorimetric detection is one example.

Conventional methods are available to bind these labels covalently to proteins or polypeptides. For instance, coupling agents such as dialdehydes, carbodiimides, dimaleimides, bis-imidates, bis-diazotized benzidine, and the like may be used to tag the antibodies with the above-described fluorescent, chemiluminescent, and enzyme labels. See, for example, U.S. Pat. No. 3,940,475 (fluorimetry) and U.S. Pat. No. 3,645,090 (enzymes); Hunter et al. *Nature* 144:945 (1962); David et al. *Biochemistry* 13:1014-1021 (1974); Pain et al. *J. Immunol. Methods* 40:219-230 (1981); and Nygren *J. Histochem. and Cytochem.* 30:407-412 (1982). In certain embodiments, labels herein are fluorescent to increase amplification and sensitivity to 8 pg/ml, more preferably biotin with streptavidin-β-galactosidase and MUG for amplifying the signal. In certain embodiments, a colorimetric label is used, e.g., where the detectable antibody is biotinylated and the detection means is avidin or streptavidin-peroxidase and 3,3',5,5'-tetramethyl benzidine.

The conjugation of such label, including the enzymes, to the antibody is a standard manipulative procedure for one of ordinary skill in immunoassay techniques. See, for example, O'Sullivan et al. "Methods for the Preparation of Enzyme-antibody Conjugates for Use in Enzyme Immunoassay," in *Methods in Enzymology*, ed. J. J. Langone and H. Van Vunakis, Vol. 73 (Academic Press, New York, N.Y., 1981), pp. 147-166.

Following the addition of last labeled antibody, the amount of bound antibody is determined by removing excess unbound labeled antibody through washing and then measuring the amount of the attached label using a detection method appropriate to the label, and correlating the measured amount with the amount of free VEGF$_{110+}$ or VEGF in the biological sample. For example, in the case of enzymes, the amount of color developed and measured will be a direct measurement of the amount of VEGF$_{110+}$ or VEGF present. Specifically, if HRP is the label, the color is detected using the substrate 3,3',5,5'-tetramethyl benzidine at 450 nm absorbance.

In one example, after an enzyme-labeled second antibody directed against the first unlabeled antibody is washed from the immobilized phase, color or chemiluminescence is developed and measured by incubating the immobilized capture reagent with a substrate of the enzyme. Then the amount of free VEGF$_{110+}$ or VEGF concentration is calculated by comparing with the color or chemiluminescence generated by the standard VEGF run in parallel.

Kits

As a matter of convenience, the assay method of this invention can be provided in the form of a kit. Such a kit is a packaged combination including the basic elements of:

(a) capture reagent comprised of the monoclonal antibody against human VEGF molecule, wherein the monoclonal antibody recognizes VEGF$_{110+}$; and (b) detection reagents comprised of detectable (labeled or unlabeled) antibodies that bind to the KDR and FLT1 receptor binding domains of VEGF. These basic elements are defined hereinabove. In certain embodiment, the detection reagents comprise a detectable antibody(ies) that bind to epitope of VEGF1-110.

Preferably, the kit further comprises a solid support for the capture reagents, which may be provided as a separate element or on which the capture reagents are already immobilized. Hence, the capture antibodies in the kit may be immobilized on a solid support, or they may be immobilized on such support that is included with the kit or provided separately from the kit.

Preferably, the capture reagents are coated on a microtiter plate. The detection reagent may be labeled antibodies detected directly or unlabeled antibodies that are detected by labeled antibodies directed against the unlabeled antibodies raised in a different species. Where the label is an enzyme, the kit will ordinarily include substrates and cofactors required by the enzyme, and where the label is a fluorophore, a dye precursor that provides the detectable chromophore. Where the detection reagent is unlabeled, the kit may further comprise a detection means for the detectable antibodies, such as the labeled antibodies directed to the unlabeled antibodies, preferably in a fluorimetric-detected format. Where the label is an enzyme, the kit will ordinarily include substrates and cofactors required by the enzyme, where the label is a fluorophore, a dye precursor that provides the detectable chromophore, and where the label is biotin, an avidin such as avidin, streptavidin, or streptavidin conjugated to HRP or β-galactosidase with MUG.

In one specific embodiment, the capture reagent is monoclonal antibody, preferably rodent, more preferably murine or rat, still more preferably murine, and most preferably MAb 5C3. Also in certain embodiments, the detectable antibody is a biotinylated monoclonal antibody, the monoclonal antibody is rodent, more preferably murine or rat, still more preferably murine, yet still more preferably MAb A4.6.1. In certain embodiments, the capture reagent is immobilized in this kit.

In certain embodiments, the kit can contain multiple ELISA for comparison studies as described herein for detecting various forms of VEGF and $VEGF_{110+}$.

The kit also typically contains instructions for carrying out the assay, and/or VEGF as an antigen standard (e.g., purified VEGF, preferably recombinantly produced VEGF, and VEGF110), as well as other additives such as stabilizers, washing and incubation buffers, and the like.

Examples of standards for VEGF are recombinant human VEGF produced in mammalian cells available from Genentech, Inc., South San Francisco, Calif., and from those companies and processes described herein.

The components of the kit will be provided in predetermined ratios, with the relative amounts of the various reagents suitably varied to provide for concentrations in solution of the reagents that substantially maximize the sensitivity of the assay. Particularly, the reagents may be provided as dry powders, usually lyophilized, including excipients, which on dissolution will provide for a reagent solution having the appropriate concentration for combining with the sample to be tested.

Deposit of Materials

The following material has been deposited with the American Type Culture Collection, 10801 University Boulevard, Manassas, Va. 20110-2209, USA (ATCC): 5C3.1.1 was deposited with the ATCC under accession number PTA-7737 deposited on Jul. 19, 2006.

| Hybridoma | ATCC Accession No. | Deposit Date |
| --- | --- | --- |
| 5C3.1.1 | PTA-7737 | Jul. 19, 2006 |
| A4.6.1 | HB10709 | Mar. 29, 1991 |

The deposit was made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposits will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The specification is considered to be sufficient to enable one skilled in the art to practice the invention. The invention is not to be limited in scope by the construct deposited, since the deposited embodiment is intended as a single illustration of certain aspects of the invention and any constructs that are functionally equivalent are within the scope of the invention. The deposit of material herein does not constitute an admission that the written description is inadequate to enable the practice of any aspect of the invention, including the best more thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Example 1

Vascular endothelial growth factor (VEGF), which is expressed as different isoforms due to alternative RNA splicing, is known to play a key role in tumor angiogenesis. We measured the concentrations of $VEGF_{165}$ and total VEGF and evaluated the relative amount of $VEGF_{110}$, which is an active fragment generated by plasmin digestion of VEGF. ELISA A (VEGF165-206 ELISA) detects $VEGF_{165}$ and longer isoforms but not $VEGF_{121}$. ELISA B (VEGF110-206 ELISA) detects $VEGF_{165}$ and isoforms, $VEGF_{121}$ and $VEGF_{110}$. ELISA C (VEGF121-206 ELISA) detects $VEGF_{165}$ and longer isoforms, $VEGF_{121}$ and VEGF fragments with molecular weight larger than $VEGF_{110}$ but not $VEGF_{110}$ (referred to herein as "$VEGF_{110+}$").

Materials and Methods

Reagents and cells: Recombinant $VEGF_{165}$ (Genentech), $VEGF_{121}$ (PeproTech, Rocky Hill, N.J.), $VEGF_{8-109}$ (consisting of amino acids 8-109 of $VEGF_{165}$) and truncated $VEGF_{121}$ (R&D Systems, Minneapolis, Minn.) were produced in *E. coli*. Truncated $VEGF_{121}$ has an intact N-terminus by mass spectrometry but has a mass of 26 KDa, consistent with truncation of approximately nine amino acids from the carboxy-terminus according to the manufacturer. It migrated between $VEGF_{110}$ and $VEGF_{121}$ when analyzed by SDS-PAGE under reducing conditions. $VEGF_{110}$ was prepared by plasmin digestion of $VEGF_{165}$ (Keyt B A, et al.: *The carboxyl-terminal domain (111-165) of vascular endothelial growth factor is critical for its mitogenic potency. J Biol. Chem.* 271: 7788-7795 (1996)). The molecular weight measured by mass spectrometry was 25390, matching the theoretical mass of 25389. The concentration was determined using bicinchorinic acid method (Pierce, Rockford, Ill.). Molecular weights used for concentration calculation of $VEGF_{8-109}$, $VEGF_{121}$ and $VEGF_{165}$ were 23.8, 28.9 and 38.2 KDa, respectively. Monoclonal anti-VEGF antibodies A4.6.1, 3.5F8, 2E3 and 5C3 were generated by immunizing mice with $VEGF_{165}$ produced in CHO cells (Kim K J, et al.: *The vascular endothelial growth factor proteins: Identification of biologically relevant regions by neutralizing monoclonal antibodies. Growth Factors* 7: 53-64 (1992)). Breast cell lines SK-BR-3, BT-474, T-47D and MCF-7 as well as ovarian cell lines ES-2, OVCAR-3 and SK-OV-3 (American Type Culture Collection, Rockville, Md.) were grown in RPMI, 2 mM L-glutamine and 10% FBS (except 20% for OVCAR-3) in a humidified 5% $CO_2$ incubator at 37° C.

Purification of VEGF in conditioned media of A673 cells: A673 cells (American Type Culture Collection) were grown in 50:50 F12/DMEM, 2 mM L-glutamine and 5% FBS to 60% confluency and then in serum free medium (Genentech) till confluency. VEGF was purified from the supernatants using an A4.6.1-Sepharose column that was prepared with CNBr activated Sepharose (Amersham Biosciences, Piscataway, N.J.). The column eluate and recombinant VEGF controls (0.2 µg per lane) were run on a 18% Tris-Glycine gels (Invitrogen, Carlsbad, Calif.) under reducing conditions and were blotted unto nitrocellulose. The blot was blocked with 0.5M Tris-HCl, pH 7.5, 1.5M NaCl, 50 mM EDTA, 0.5% Trition100 containing 3% bovine serum albumin and probed with 200 ng/ml of 3.5F8 or A4.6.1 followed by 2 ng/ml of goat anti-mouse Fc-HRP (Jackson ImmunoResearch). Signals were developed using SuperSignal West Dura (Pierce) and recorded on X-ray film.

VEGF ELISAs for Measuring VEGF Concentrations

ELISA A (VEGF165-206 ELISA). Unless otherwise mentioned, a fluorometric ELISA A was used for measuring VEGF in samples. The fluorimetric ELISA A used 3.5F8 for coat and biotinylated A4.6.1 followed by streptavidin-β galactosidase for detection and 4-methylumbelliferyl-β-D galactoside as the substrate (Rodriguez C R, et al.: *A sensitive fluorometric enzyme-linked immunosorbent assay that measures vascular endothelial growth factor165 in human plasma. J Immunol Methods* 219: 45-55 (1998)). The $VEGF_{165}$ standards were 1-128 pg/mL, or 0.026-3.35 pM. The colorimetric ELISA A used 3.5F8 for coat and biotinylated A4.6.1 for detection, following the protocol used for the ELISA C described below. The $VEGF_{165}$ standards were 1.6-200 pg/mL.

ELISA B (VEGF110-206 ELISA) (previously named VEGF121-206 ELISA, Konecny G E, et al.: *Association between HER-2/neu and Vascular Endothelial Growth Factor Expression Predicts Clinical Outcome in Primary Breast Cancer Patients. Clinical Cancer Research,* 10: 1706-1716 (2004)): MaxiSorp 96-well microwell plates were coated with 0.5 µg/ml antibody A4.6.1 in 50 mM carbonate buffer, pH 9.6 at 100 µl/well at 4° C. overnight. Plates were washed after this step and between the subsequent room temperature incubation steps with PBS, pH 7.4, containing 0.05% polysorbate 20. Plates were blocked with 0.5% bovine serum albumin, 10 ppm Proclin™ 300 (Supelco, Bellefonte, Pa.) in PBS (150 µl/well) for 1 h. VEGF standards (1.56-200 pg/ml $VEGF_{165}$ or 0.0409-5.24 pM VEGF in twofold serial dilution) and serially diluted samples (minimum 1:10 dilution) in twofold or threefold serial dilution in PBS, pH 7.4, containing 0.5% bovine serum albumin, 0.05% polysorbate 20, 5 mM EDTA, 0.25% CHAPS, 0.2% bovine γ-globulins (Sigma, St. Louis, Mo.) and 0.35 M NaCl (sample buffer) were added to the plates (100 µl/well) and incubated for 2 h. Bound VEGF was detected by incubating biotinylated 2E3 (or another antibody that binds to a receptor binding domain of VEGF) on the plates for 1 h followed by streptavidin-HRP (Amersham, Copenhagen, Denmark) for 30 min, biotinyl-tyramide (ELAST ELISA amplification System, Perkin Elmer Life Sciences Inc., MA) for 15 min and streptavidin-HRP for 30 min. The substrate TMB (3,3',5,5'-tetramethyl benzidine) (Kirkegaard & Perry Laboratories) was added and the reaction was stopped by adding 1 M phosphoric acid. Absorbance was read at 450 nm on a Titertek stacker reader (ICN, Costa Mesa, Calif.). The titration curves were fit using a four-parameter regression curve-fitting program (KaleidaGraph, Synergy software, Reading, Pa.). Data points which fell in the range of the standard curve were used for calculating the putative VEGF concentrations in the samples. The recovery of 1.56-200 pg/ml $VEGF_{165}$ in 10% human EDTA plasma (Golden West Biologicals Inc., Temecula, Calif.) was 92-120% after subtracting the putative 2.1 pg/ml endogenous VEGF in the 10% plasma used for this study.

ELISA C (VEGF121-206 ELISA): Microwell plates were coated with 1 µg/ml anti-VEGF 5C3 antibody and blocked as described above. VEGF standards (4.00-512 pg/ml $VEGF_{165}$ or 0.105-13.4 pM VEGF in 2-fold serial dilution) and serially diluted samples in sample buffer were added to the plates. The plates were incubated for 2 h. Bound VEGF was detected by adding biotinylated A4.6.1 followed by streptavidin-HRP and TMB as the substrate. Plates were read and data were analyzed as described above. The recovery of 4.00-512 pg/ml $VEGF_{165}$ in 10% plasma was 77-101% after subtracting 1.6 pg/ml putative endogenous VEGF in the 10% plasma used for this study.

Results and Discussion

Figure 1B:
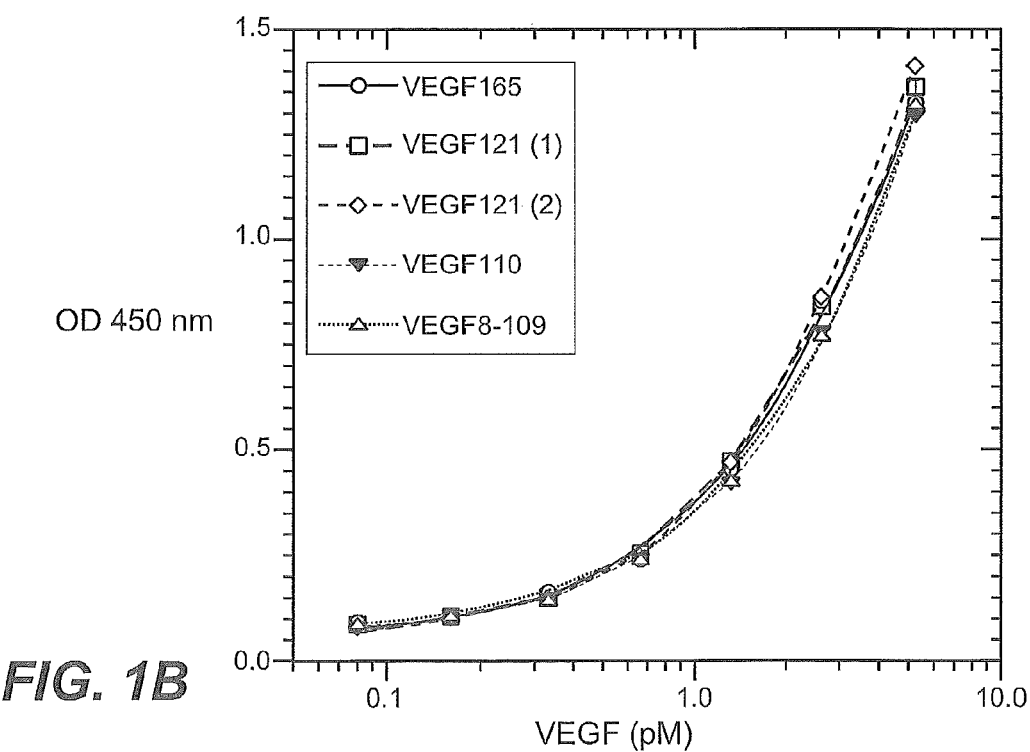
Figure 1C:
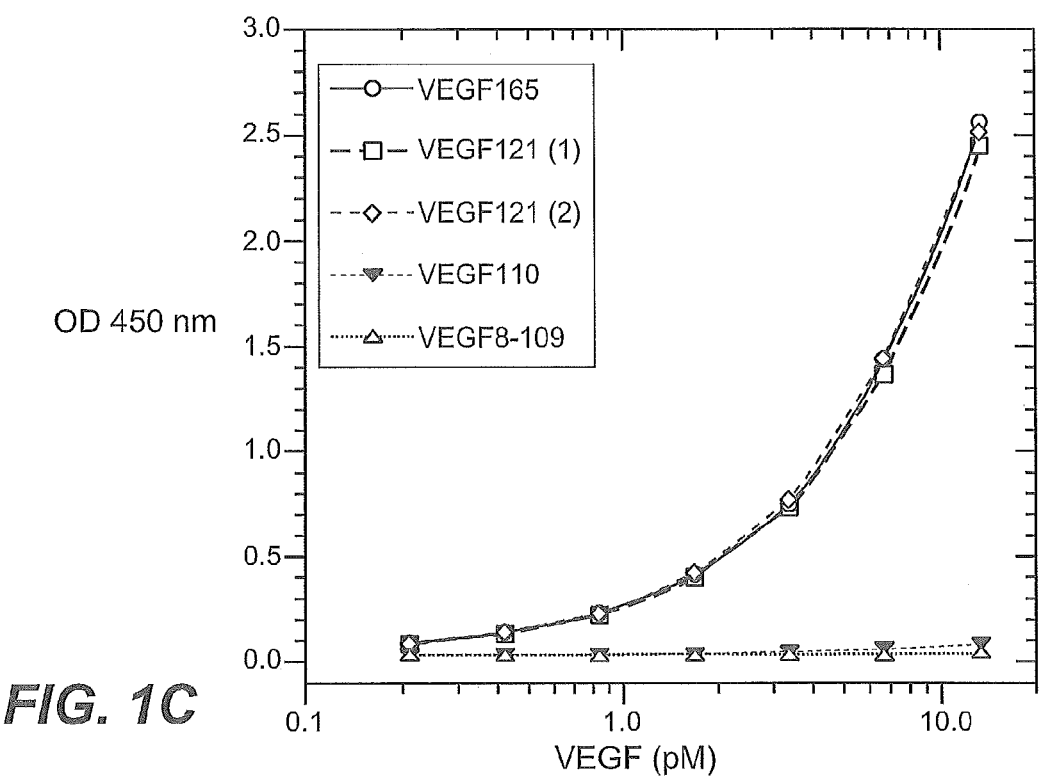
Figure 3:
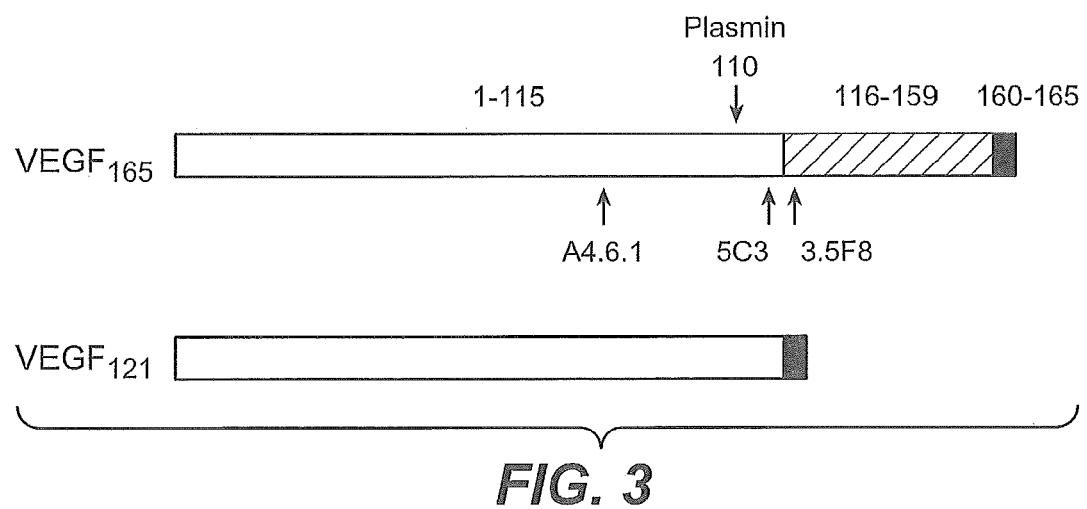
FIG. 3 illustrates a diagram of $VEGF_{165}$, $VEGF_{121}$ and $VEGF_{110}$ (N-terminal fragment generated by plasmin digestion of VEGF) showing the proposed binding sites of the antibodies used in the three VEGF ELISAs.

VEGF ELISAs: The previously described ELISA A uses 3.5F8 for coat and biotinylated A4.6.1 for detection (Rodriguez C R, et al.: *A sensitive fluorometric enzyme-linked immunosorbent assay that measures vascular endothelial growth factor165 in human plasma. J Immunol Methods* 219: 45-55, 1998). It detects VEGF165 ($VEGF_{165}$) but not VEGF121(1) ($VEGF_{121}(1)$), which is from R&D systems and missing approximately 9 amino acids from the carboxyterminus, and VEGF121(2) ($VEGF_{121}(2)$), which is from PeproTech (FIG. 1A). 3.5F8 binds $VEGF_{165}$ but not $VEGF_{121}$ by BIAcore. A4.6.1 binds to the receptor binding domain (Kim K J, et al.: *The vascular endothelial growth factor proteins: Identification of biologically relevant regions by neutralizing monoclonal antibodies. Growth Factors* 7: 53-64, 1992) that is present in all isoforms and in $VEGF_{110}$. 3.5F8 likely binds near amino acids 116 and 118, which are not present in $VEGF_{121}$. 5C3 likely binds near amino acids 111-113, which are not present in $VEGF_{110}$ (FIG. 3). ELISA A can likely detect VEGF isoforms which contained $VEGF_{165}$ sequences including $VEGF_{183}$, $VEGF_{189}$ and $VEGF_{206}$ (see, e.g., Stimpfl M, et al.: *Vascular Endothelial growth factor splice variants and their prognostic value in breast and ovarian cancer. Clinical Cancer Research* 8: 2253-2259, 2002). ELISA B (previously named VEGF121-206 ELISA, Konecny G E, et al., *Association between HER-2/neu and Vascular Endothelial Growth Factor Expression Predicts Clinical Outcome in Primary Breast Cancer Patients. Clinical Cancer Research,* 10: 1706-1716, 2004) uses A4.6.1 for coat and biotinylated 2E3 for detection. A4.6.1 and 2E3 bind to the receptor binding domain that is present in all three molecules. See, e.g., Kim K J, et al. *The vascular endothelial growth factor proteins: Identification of biologically relevant regions by neutralizing monoclonal antibodies. Growth Factors* 7:53-64 (1992); and, Muller Y A, et al. *Vascular endothelial growth factor: Crystal structure and functional mapping of the kinase domain receptor binding site. Proc Natl Acad Sci USA* 94:7192-7197 (1997). Other antibodies that bind in these regions can also be used. This ELISA detects $VEGF_{165}$, $VEGF_{121}$, truncated $VEGF_{121}$ (missing approximately 9 amino acids from the carboxy-terminus), $VEGF_{110}$ and $VEGF_{8-109}$ equally well (FIG. 1B). This ELISA can detect total VEGF, including fragments larger than $VEGF_{110}$ generated by matrix metalloproteinase digestion. ELISA C, described herein, which uses 5C3 for coat and biotinylated A4.6.1 for detection, detects $VEGF_{165}$, $VEGF_{121}$, and truncated $VEGF_{121}$ equally well but does not detect $VEGF_{110}$ or $VEGF_{8-109}$ (FIG. 1, C). 5C3 binds $VEGF_{121}$ but not $VEGF_{8-109}$ by BIAcore. This ELISA can detect all the VEGF molecules detected by the $VEGF_{110-206}$ except $VEGF_{110}$ and smaller fragments.

The sensitivities of ELISA A, ELISA B and ELISA C were 10, 16 and 40 pg/ml $VEGF_{165}$ (or 0.26, 0.41 and 1.05 pM for different VEGF isoforms and fragments) for VEGF in samples using a minimum 1:10 dilution, respectively. ELISA B and ELISA C were reproducible (Table 1 & 2). ELISA B and ELISA C were specific to VEGF (VEGF-A). VEGF-B, VEGF-C and VEGF-D at concentrations up to 50 ng/ml only gave background signals. Insulin-like growth factor 1, growth hormone, recombinant nerve growth factor, tumor necrosis factor (Genentech), platelet-derived growth factor AB, placenta growth factor, transforming growth factor β1 (R&D Systems) (up to 200 ng/ml) only gave background signals. Heparin (Leo Laboratories, Bucks, UK and Dublin, Ireland) (up to 100 U/ml) did not have a significant effect on the assay.

TABLE 1

ELISA B ($VEGF_{110-206}$ ELISA): The standard range was 1.56-200 pg/ml $VEGF_{165}$ (0.0409-5.24 pM VEGF) in buffer.

| Control[a] | Mean (pg/ml) | Inter % CV | Intra % CV |
|---|---|---|---|
| Low | 3.07 | 17.7 | 13.5 |
| Middle | 38.0 | 9.50 | 6.54 |
| High | 127 | 9.11 | 6.95 |

The OD ratio of 1.56 pg/ml standard relative to the blank was 1.37 ± 0.11.
CV is coefficient of variation.
[a]The middle and high controls were made by spiking recombinant $VEGF_{165}$ into human EDTA plasma. The low control was made by spiking $VEGF_{165}$ into 70% plasma since plasma contained endogenous VEGF. Controls were diluted 1:10 and assayed in duplicate in 34 independent assays.

TABLE 2

ELISA C ($VEGF_{121-206}$ ELISA). The standard range was 4.00-512 pg/ml $VEGF_{165}$ (0.105-13.4 pM VEGF).

| Control | Mean (pg/ml) | Inter % CV | Intra % CV |
|---|---|---|---|
| Low | 3.28 | 20.6 | 8.35 |
| Middle | 11.7 | 6.56 | 2.39 |
| High | 56.5 | 2.57 | 1.37 |

The OD ratio of 4 pg/ml standard relative to the blank was 2.72 ± 0.37.
CV is coefficient of variation.
[a]The controls were made by spiking recombinant $VEGF_{165}$ into human EDTA plasma. They were diluted 1:10 and assayed in duplicate in 15 independent assays.

VEGF in conditioned media of cell lines: Conditioned media from six stable CHO clones transfected with $VEGF_{165}$ cDNA (Meng et al., 2000) were measured by the three ELISAs, which used non-glycosylated VEGF produced in *E. coli* as standard. Glycosylated recombinant $VEGF_{165}$ in conditioned media from six stable CHO clones gave very similar concentrations in the three ELISAs. Concentrations measured by ELISA B were 28, 63, 64, 43, 3.8 and 3.2 nM, respectively. Ratios of VEGF concentrations measured by ELISA A and ELISA C compared to those by ELISA B were 0.90±0.08 and 1.08±0.10, respectively. Therefore, the three ELISAs quantitated glycosylated VEGF equally well and there was little proteolysis of $VEGF_{165}$ under the culture conditions.

Figure 2:
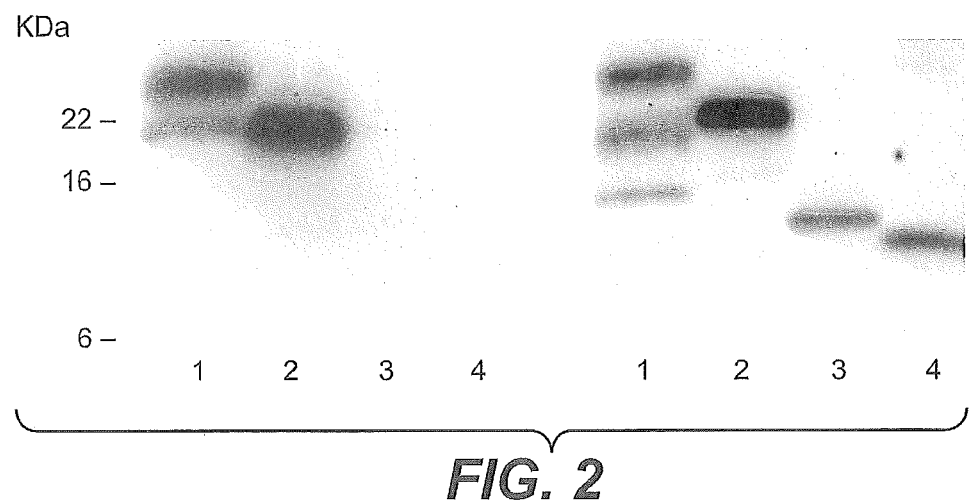
FIG. 2 illustrates protein blotting of VEGF produced by A673 cells, using 3.5F8 (left) or A4.6.1 (right) for probing. Samples are VEGF purified from conditioned medium of A673 cells using an A4.6.1 Affinity column (lane 1) and recombinant VEGF proteins $VEGF_{165}$, $VEGF_{121}$ (likely missing approximately 9 amino acids from the carboxy-terminus according to the manufacturer, R&D systems) and $VEGF_{8-109}$ produced by *E. coli* (lanes 2, 3 and 4, respectively).

VEGF concentrations in A673 cell conditioned medium measured by ELISA A, ELISA B and ELISA C were 0.15, 0.29 and 0.24 nM VEGF, respectively. The concentration measured by ELISA A was lower, indicating $VEGF_{121}$ was present. When VEGF was purified from conditioned medium using an A4.6.1 affinity column and analyzed by protein blotting, two bands, likely glycosylated and non-glycosylated $VEGF_{165}$ were detected by 3.5F8. The lower band had the same mobility as the purified $VEGF_{165}$ produced in *E. coli* (FIG. 2, left). N-glycanase treatment converted the upper band to the lower band. Two additional lower molecular weight bands, likely glycosylated (partially overlapping with the putative non-glycosylated $VEGF_{165}$ band) and non-glycosylated $VEGF_{121}$ were detected by A4.6.1 (FIG. 2, right). The lower band had the same mobility as the purified $VEGF_{121}$ produced in *E. coli* and N-glycanase treatment converted the upper band to the lower band.

VEGF concentrations in conditioned media from breast cell lines SK-BR-3, BT-474, T-47D and MCF-7 measured by ELISA B were 3.6, 16, 13, and 13 pM, respectively. Ratios of VEGF concentrations measured by ELISA A to those by ELISA B were 0.49, 0.42, 0.43 and 0.38 (or 49%, 42%, 43% or 38%), respectively, in agreement with 43, 35, 40 and 41% of $VEGF_{165}$ expression in these respective cell lines (Stimpfl M, et al.: *Vascular Endothelial growth factor splice variants and their prognostic value in breast and ovarian cancer.* Clinical Cancer Research 8: 2253-2259, 2002). Ratios of VEGF concentrations measured by ELISA C to those by ELISA B were 1.1-1.2 for these cell lines, indicating that little $VEGF_{110}$ was present. VEGF concentrations in conditioned media from ovarian cell lines ES-2, OVCAR-3 and SK-OV-3 measured by ELISA B were 32, 11 and 20 pM, respectively. Ratios of VEGF concentrations measured by ELISA A to those by ELISA B were 0.24, 0.20, and 0.32 (or 24%, 20% and 32%), respectively, compared to 38, 42 and 24% of $VEGF_{165}$ expression in these respective cell lines (Stimpfl et al., supra). Ratios of VEGF concentrations measured by ELISA C to those by ELISA B were 0.64-0.79 for these cell lines, indicating $VEGF_{110}$ (or smaller fragments) may be present.

We claim:

1. An antibody 5C3 produced by hybridoma 5C3.1.1 deposit number PTA-7737.

2. The antibody of claim 1 conjugated to a detectable label.

3. A hybridoma 5C3.1.1 deposited under ATCC deposit number PTA-7737.

* * * * *

UNITED STATES PATENT AND TRADEMARK OFFICE
CERTIFICATE OF CORRECTION

PATENT NO.           : 8,449,885 B2  
APPLICATION NO.      : 12/817827  
DATED                : May 28, 2013  
INVENTOR(S)          : Yu-Ju G. Meng, Kyu H. Hong and Johnny Gutierrez Page 1 of 1

It is certified that error appears in the above-identified patent and that said Letters Patent is hereby corrected as shown below:

On Title Page 2, column 2, line 41, Other Publications, replace "Article (4(3) EPC" with --Article 94(3) EPC--.

In the Specification  
Column 10, Line 23, replace "V is Sci" with --Vis Sci--.

Signed and Sealed this  
First Day of July, 2014

Michelle K. Lee  
*Deputy Director of the United States Patent and Trademark Office*